United States Patent [19]

Seeger

[11] Patent Number: 5,334,525

[45] Date of Patent: Aug. 2, 1994

[54] HEPADNAVIRUS POLYMERASE GENE PRODUCT HAVING RNA-DEPENDENT DNA PRIMING AND REVERSE TRANSCRIPTASE ACTIVITIES AND METHODS OF MEASURING THE ACTIVITIES THEREOF

[75] Inventor: Christoph Seeger, Melrose Park, Pa.

[73] Assignee: Fox Chase Cancer Center, Philadelphia, Pa.

[21] Appl. No.: 937,214

[22] Filed: Aug. 28, 1992

[51] Int. Cl.$^5$ .............. C12N 9/12; C12N 15/10; C08L 5/00; C12Q 1/48

[52] U.S. Cl. .................. 435/194; 435/6; 435/15; 435/69.1; 435/91.51; 935/14; 935/17; 252/183.11; 536/23.2; 536/23.72

[58] Field of Search ............ 435/194, 69.1, 6, 15, 435/91.51; 935/14, 17; 252/183.11; 536/23.2, 23.72

[56] References Cited

U.S. PATENT DOCUMENTS 4,937,074  6/1990  Venkateswaran et al. ...... 424/195.1
4,968,674  11/1990 Taniyama et al. .............. 514/63
4,997,926  3/1991  Haertle et al. ................ 536/27.14

FOREIGN PATENT DOCUMENTS 343133    11/1989  European Pat. Off. .
WO8800050 11/1988  PCT Int'l Appl. .
WO9214839 9/1992   PCT Int'l Appl. .

OTHER PUBLICATIONS

G. G. Lin et al. "Evidence for Involvement of a Ribosomal Leaky . . . " Virology 188:342–352 (May 1992).
E. McGlynn et al. "Hepatitis B Virus Polymerase Gene: Expression . . . " J. Gen. Virol. 73(6) 1515–1519 (Jun. 1992).
H. G. Kochel et al. "Identification of a Binding Site in the Hepatitis . . . " Virology 182(1) 94–101 (May 1991).
G. R. Foster et al. "Expression of the terminal protein region of Hepatitis . . . " Proc. Natl. Acad. Sci. 88:2888–2892 (Apr. 1991).
R. Bartenschlager et al. "Expression of the P-protein of the Human . . . " Nuc. Acids Res. 20(2) 195–202 (Jan. 1992).
T. Wu et al., J. Virol. 65: 2155–2163 (1991).
H. Meisel et al., J. Med. Virol., 30: 137–141 (1990).
L. Chang et al., J. Virol. 64: 5553–58 (1990).
G. Civitico et al., J. Med. Virol., 31: 90–97 (1990).
W. Offensperger et al., Virology, 164: 48–54 (1988).
H. Lin et al., J. Med. Virol. 12: 61–70 (1983).
C. Howard, J. Med. Virol., 3: 81–86 (1978).
P. L. Marion, Current Topics in Microbiology and Immunology, 168: 168–183 (1991).
M. Bavand et al., Journal of Virology, 63: 1019–1021 (1989).
E. Mandart et al., Journal of Virology, 49: 782–792 (1984).
J. C. Pugh et al., Journal of Virology, 62: 3513–3516 (1988).
L. Chang et al., Nature, 337: 364–368 (1989).
H. Schlicht, Cell, 56: 85–92 (1989).
M. Bavand et al., Journal of Virology, 62: 626–628 (1988).

Primary Examiner—Robert A. Wax
Assistant Examiner—Rebecca Prouty
Attorney, Agent, or Firm—Dann, Dorfman, Herrell and Skillman

[57] ABSTRACT

An enzymatically active, substantially virus-free hepadnavirus polymerase gene product is provided, which possesses a DNA priming function and reverse transcriptase activity, both of which are dependent on the presence of an RNA template and magnesium ions. The hepadnavirus polymerase gene product is produced by in vitro transcription and translation of a hepadnavirus pol gene.

The enzymatically active hepadnavirus polymerase gene product is used in rapid in vitro assays to screen potential anti-hepadnaviral agents. An assay for the DNA priming activity of the gene product is provided, wherein covalent attachment of labelled dGTP to the gene product is quantitatively measured. An assay for the reverse transcriptase activity of the gene product is provided, wherein incorporation of nucleotide triphosphates into the nascent DNA minus strand is measured, taking advantage of the covalent attachment of said nascent strand to the polymerase gene product.

18 Claims, 2 Drawing Sheets

HEPADNAVIRUS POLYMERASE GENE PRODUCT HAVING RNA-DEPENDENT DNA PRIMING AND REVERSE TRANSCRIPTASE ACTIVITIES AND METHODS OF MEASURING THE ACTIVITIES THEREOF

Pursuant to 35 U.S.C. § 202(c), it is hereby acknowledged that the U.S. Government has certain rights in the invention described herein, which was made in part with funds from the National Institutes of Health.

FIELD OF THE INVENTION

The present invention relates to the development of anti-vital therapy for chronic hepadnavirus infection. In particular, the invention relates to a hepadnavirus polymerase gene product, produced in vitro and having RNA-dependent DNA priming and reverse transcriptase activities, and to the use of said gene product for rapid in vitro assays to screen potential anti-viral agents.

BACKGROUND OF THE INVENTION

Hepatitis B is a life-threatening disease that affects millions of individuals worldwide. Several vaccines are currently available to prevent initial infection with the hepatitis B virus (HBV). However, many patients become chronically infected with the virus, becoming potential sources of spread of the disease, and suffering the high risk of liver ailments associated with long-term infection, such as chronic hepatitis, cirrhosis and hepatocellular carcinoma.

Chronic hepadnavirus infection is extremely difficult to eradicate for several reasons: (1) chronically infected patients develop immunotolerance to vital surface antigens; (2) the hepatitis B virus does not kill host hepatocytes, so vital infection cannot be overcome simply by preventing new infection and allowing already-infected host cells to die; (3) the covalently closed circular form of the hepadnavirus genome does not self-replicate and is therefore unaffected by agents which inhibit DNA-directed DNA synthesis; (4) hepatitis B virus exists in non-hepatic tissues, so reinfection of hepatic tissue may result from virus located in other tissues; and (5) the hepadnavirus genome can integrate into hepatocyte chromosomes, and thus exist in a dormant, non-replicative form for many years. See P. L. Marion, Current Topics in Microbiology and Immunology, Vol. 168: 167–183 (1991). In spite of these obstacles, certain steps in the replication cycle of hepadnaviruses have been cited as potential targets for anti-viral therapy. One potential target is the replication of the hepadnavirus genome by reverse transcription of the RNA pregenome. This step is essential in the life cycle of the virus.

Reverse transcription of the RNA pregenome is catalyzed by a gene product encoded by the hepadnavirus pol gene. The pol gene encodes three activites: (1) DNA priming activity; (2) reverse transcriptase (i.e., RNA-directed DNA polymerase) activity; and (3) RNAse H activity. It has heretofore not been known whether these three catalytic functions are embodied in one or several separate gene products. In fact, little is known about the product or products of the viral pol gene, and this lack of knowledge has frustrated attempts to develop anti-viral agents targeted to the pol gene product.

Efforts to obtain more detailed information about the mechanism and biochemistry of the reactions directing reverse transcription of the hepadnavirus genome have been stymied by the inability to obtain enzymatically active hepadnavirus polymerase gene product. See, e.g., Bayand et al., J. Virol., 63: 1019–21 (1989). Consequently, there has been no feasible means to study or screen for anti-viral agents directed toward this protein or set of proteins. Thus, a potentially useful target for anti-viral therapy has remained virtually unexplored. A need clearly exists for the production of a purified hepadnavirus polymerase gene product that can be used for in vitro assays to screen for potential anti-viral agents. A concomitant need exists for methods to measure the various activities of such a gene product, once it becomes available.

SUMMARY OF THE INVENTION

In accordance with the present invention, an enzymatically active, substantially virus-free hepadnavirus polymerase gene product is provided. The hepadnavirus gene product possesses a DNA priming activity and a reverse transcriptase activity, both of which are independent of other hepadnaviral gene products, and both of which are dependent on the presence of magnesium ions and an RNA template for hepadnavirus minus strand DNA synthesis. The template comprises an initiation site for the minus strand DNA synthesis.

According to another aspect of the present invention, the enzymatically active hepadnavirus polymerase gene product is produced by expression, in a non-hepadnavirus system, of a purified and isolated DNA sequence encoding the hepadnavirus polymerase gene product. Expression of the polymerase gene product-encoding DNA sequence is preferably accomplised by in vitro transcription of the DNA sequence, followed by in vitro translation of the resulting RNA transcript, thereby forming the enzymatically active hepadnavirus polymerase gene product.

According to another aspect of the present invention, a rapid, in vitro method for measuring the DNA priming activity of a hepadnavirus polymerase gene product is provided. The method comprises the steps of: (1) providing the above-described enzymatically active, substantially virus-free hepadnavirus gene product; (2) combining, in an assay buffer containing magnesium ions, the gene product with an RNA template for hepadnavirus minus strand DNA synthesis, the template comprising an initiation site for minus strand synthesis, and a detectably-labelled nucleotide triphosphate comprising the first nucleotide incorporated into the hepadnavirus minus strand DNA (usually dGTP), under conditions promoting the DNA priming activity of the polymerase gene product, resulting in the formation of a complex comprising the gene product and the detectably labelled nucleotide triphosphate; (3) separating the complex from the assay buffer; and (4) detecting the amount of the detectably-labelled nucleotide triphosphate in the separated complex.

According to another aspect of the present invention, the above-described method for measuring the DNA priming activity of a hepadnavirus polymerase gene product is adapted to a rapid, in vitro method of screening potential anti-hepadnaviral agents for the ability to inhibit such DNA priming activity.

According to yet another aspect of the present invention, a rapid, in vitro method for measuring the reverse transcriptase activity of a hepadnavirus polymerase gene product is provided. The method comprises: (1) providing the above-described enzymatically active, substantially virus-free hepadnavirus polymerase gene product; (2) combining, in an assay buffer containing magnesium ions, the hepadnavirus polymerase gene product with an RNA template for hepadnavirus minus strand DNA synthesis, the template comprising an initiation site for minus strand DNA synthesis, and nucleotide triphosphates for DNA synthesis (one of said nucleotide triphosphates optionally being detectably labelled), under conditions promoting the reverse transcriptase activity of the polymerase gene product, thereby producing a nascent strand of DNA from the RNA template, the DNA strand being part of a complex which further comprises the polymerase gene product; (3) separating the complex from the assay buffer; and (4) detecting the amount of the nascent DNA strand in the separated complex. The length of the nascent DNA strand may also observed, which provides an additional indication of reverse transcriptase activity of the hepadnavirus polymerase gene product.

According to another aspect of the present invention, the above-described method for measuring reverse transcriptase activity of a hepadnavirus polymerase gene product is adapted to a rapid, in vitro method of screening potential anti-hepadnaviral agents for their ability to inhibit such reverse transcriptase activity.

The enzymatically active, substantially virus-free hepadnavirus polymerase gene product of the present invention, along with the rapid, in vitro assays that utilize the polymerase gene product of the invention, provide an extremely useful, and long-needed target for development of antiviral agents directed to hepadnaviruses. The compositions and methods of the present invention will allow the screening of many anti-viral compounds simultaneously, with ease and rapidity. Morover, quantitative results of the effect of each potential anti-viral agent are easily obtained. Heretofore, such results have been unobtainable.

BRIEF DESCRIPTION OF THE DRAWINGS

The foregoing summary, as well as the following description of preferred embodiments of the present invention, will be better understood when read in conjunction with the appended drawings in which:

FIG. 2 is a set of autoradiographs of in vitro translation reactions and assays for DNA priming and reverse transcriptase activities of the DHBV polymerase gene product.

DETAILED DESCRIPTION OF THE INVENTION

The hepadnavirus polymerase gene product is referred to in the art by many different names. For purposes of the present invention, the following terminology will be applied. The product of the hepadnavirus pol gene is sometimes referred to herein as "hepadnavirus polymerase gene product", "polymerase gene product", "vital gene product" or "gene product". The polymerase gene product possesses a reverse transcriptase activity, among others. This catalytic function is also sometimes referred to herein as "RNA-directed DNA polymerase activity". The polymerase gene product, when produced by in vitro transcription/translation of a hepadnavirus pol gene, may also be referred to herein as an "in vitro translation product" or "translation product". Reference to the gene product as a translation product will be made only when describing the in vitro transcription/translation of the pol gene, which is a preferred method of making the polymerase gene product of the present invention.

Figure 1:
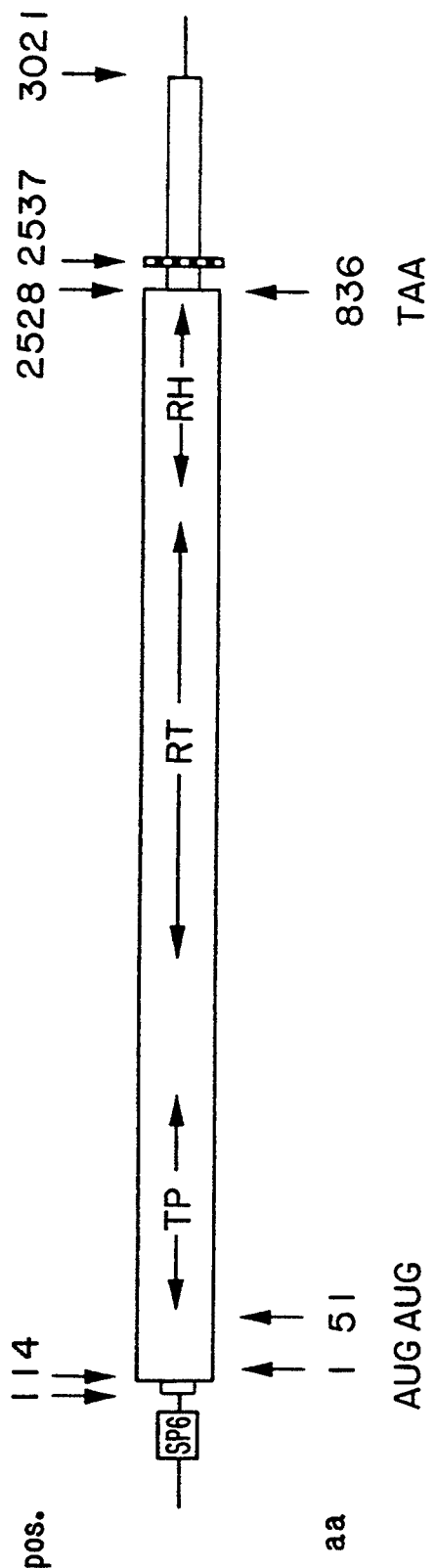
FIG. 1 is a schematic diagram of the structure and orientation of the duck hepatitis B virus (DHBV) genome, inserted into an in vitro transcription vector to form the plasmid pS.1Gal.
Figure 2A:
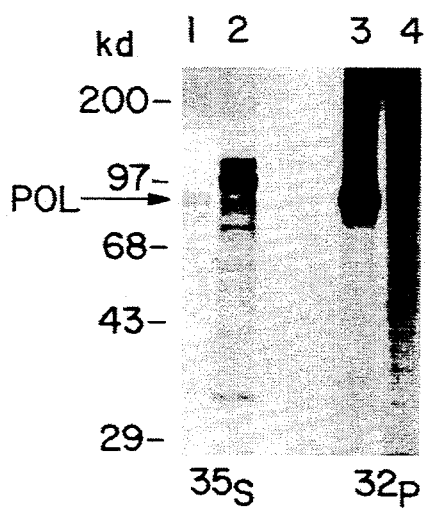
FIG. 2A: in vitro translation products (Lanes i and 2); assay of DNA priming function (Lanes 3 and 4)

In accordance with the present invention, an enzymatically active hepadnavirus polymerase gene product has now been obtained by in vitro transcription/translation of a hepadnavirus pol gene. The vital gene product was generated by SP6-promoted in vitro transcription of a plasmid containing a complete copy of an infectious duck hepatitis B virus (DHBV) genome (see FIG. 1), followed by in vitro translation of the resulting 3.1 kb RNA in a rabbit reticulocyte lysate in vitro translation system. As shown in FIG. 2A, the major in vitro translation product is a protein with an estimated molecular weight of 90 kDa, representing a 836 amino acid polypeptide (a faster-migrating translation product is also formed, presumably representing a 786 amino acid polypeptide translated from a start codon 51 amino acid downstream from the start codon of the major translation product).

Figure 2B:
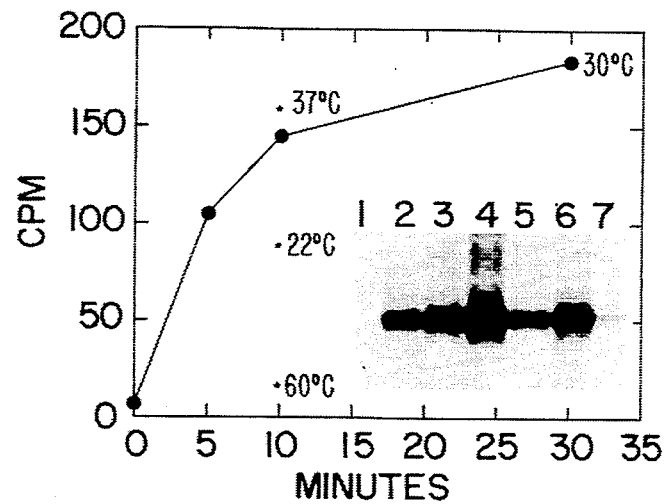
FIG. 2B: measurement of polymerase activity of DHBV polymerase gene product; graph is a quantitative representation of autoradiograph shown in inset; vertical axis = radioactivity incorporated in each band (cpm); horizontal axis = incubation time (minutes); filled circles = incubation time points at 30° C.; * = incubation temperatures at fixed, 10 minute incubation times.

As shown in FIG. 2A and 2B, the in vitro translation product was found to possess two catalytic functions: a DNA priming function and reverse transcriptase (i.e., RNA-directed DNA polymerase) activity, both of which are dependent on the presence of the RNA template present in the in vitro translation (treatment of the in vitro translation product with ribonuclease abolished both the priming and polymerase activities) and magnesium ions. The RNA dependence of the priming activity was unexpected, and could explain the failure of previous attempts by others to obtain an enzymatically active hepadnavirus polymerase gene. See, e.g., Bavand et al., supra. The in vitro translation product is also expected to possess an RNAseH activity, which is a catalytic function possessed by the gene product in vivo.

The detailed description set forth below describes preferred methods for making and using the hepadnavirus polymerase gene product of the present invention. Novel assays for measuring the various activities of the purified polymerase gene product, which rely on unique aspects of the gene product, are also described. Any molecular cloning and recombinant DNA techniques not specifically described are carried out by standard methods, as generally set forth, for example, in Sambrook et al., "DNA Cloning, a Laboratory Manual", Cold Spring Harbor Laboratory (1989).

The hepadnavirus polymerase gene product of the present invention is preferably prepared from a purified, isolated DNA molecule comprising a sequence which encodes the gene product. Thus, any hepadnavirus pol gene will provide a suitable starting material for in vitro synthesis of the gene product. These include pol genes from human hepatitis B virus (HBV), duck hepatitis B virus (DHBV) and woodchuck hepatitis virus (WHV), among others.

The pol gene can be maintained in any common cloning vector, such as a plasmid, and maintained in an appropriate host cell, such as *E. coli*. Such cloning vectors may comprise a pol gene alone, or an entire hepadnavirus genome, which contains the pol gene and other viral genes. In a preferred embodiment, a plasmid vector containing an entire infectious hepadnavirus genome, positioned downstream from a bacteriophage promoter such as SP6, T7 or T3, is utilized as the starting material for preparation of the viral polymerase gene product. In a particularly preferred embodiment, the entire genome of infectious DHBV, contained in plasmid p5.1Gal, is used to produce a DHBV polymerase gene product. This embodiment is described in greater detail in Examples 1 and 2 below.

It should be apparent to those skilled in the art that DNA and RNA are both precursors for the ultimate polymerase gene product, and that the synthesis of an RNA molecule is an intermediate step in the ultimate production of the gene product. DNA molecules are preferred as the starting material for synthesis of the polymerase gene product because of their stability, in comparison to RNA molecules, and their ease of maintenance in cloning vectors and microbial host cells. However, the DNA molecule is used to synthesize an RNA molecule, which itself can be purified and stored for use in producing the polymerase gene product.

In accordance with the present invention, the purified hepadnavirus polymerase gene product is synthesized by in vitro transcription/translation of the hepadnavirus pol gene as described above. The in vitro transcription/translation is preferably carried out in a cell-free system. For example, a pol gene or hepadnavirus genome may be inserted into an in vitro transcription vector carrying a bacteriophage promoter, such as SP6, T7 or T3. Such in vitro transcription vectors are commercially available (e.g., from Promega Biotech, Inc., Madison, Wis.). In vitro transcription may then be carried out by, e.g., an SP6 RNA polymerase, using standard methods. Kits for performing in vitro transcription are also commercially available (e.g., from Promega Biotech, Inc.). If a kit is used, in vitro transcription is performed according to the supplier's instructions.

In vitro transcription of a hepadnavirus pol gene or a hepadnavirus genome containing the pol gene results in the formation of an RNA transcript, which then may be subjected to in vitro translation to produce the polymerase gene product. It will be appreciated that the hepadnavirus gene product produced in this manner is substantially free of other hepadnaviral components, with which it would be associated in vivo.

In a preferred embodiment, the resulting transcript is a 3.1 kb RNA molecule encoding the DHBV polymerase gene product. RNA transcripts produced by in vitro transcription may be purified by standard methods and stored for later use, or they may be used immediately for in vitro translation. In either event, in vitro translation of polymerase gene transcript may be performed in commercially-available cell free translation systems, such as the rabbit reticulocyte lysate system or the wheat germ system, both commercially available (Promega Biotech, Madison, Wis.) according to the supplier's instructions. In a preferred embodiment, the RNA transcript of a DHBV pol gene, as described above, is utilized for in vitro translation in a rabbit reticulocyte lysate system. The resultant translation product is a ~90 kDa polypeptide having RNA-dependent DNA priming and reverse transcriptase activities. The SP6-promoted in vitro translation of the DHBV RNA transcript in a rabbit reticulocyte lysate system is described in greater detail in Example 2 below.

In vitro translation reaction mixtures, comprising the hepadnavirus pol gene RNA transcript and the polymerase gene product, may be used immediately for the activity assays described below, without further processing. Alternatively, the reaction mixtures, containing both the RNA template and the gene product, may be stored at $-70°$ C. for future use. It is preferred to use the in vitro translation mixture without further purification of the gene product, because the mixture already contains the RNA transcript encoding the gene product, which also serves as the template required for the priming and reverse transcriptase activity of the product.

In the event that further purification of the polymerase gene product is desired, the protein may be purified from the other components of the in vitro translation mixture by any common method, e.g., by immunological means or by various column chromatography steps. The purified polypeptide may then be used immediately, or stored frozen for future use. It should be apparent to those skilled in the art, however, that if the gene product is purified away from the RNA transcript encoding it, the transcript, or another appropriate RNA template, must be added back when assaying for the template-dependent priming or reverse transcriptase activities of the gene product.

The hepadnavirus polymerase gene product may also be synthesized from the pol gene or from intact vital genomes by coupled in vitro transcription/translation in a procaryotic or eucaryotic cellular system. If this alternative is selected, the pol gene or viral genome containing the pol gene is placed in an appropriate expression vector, many of which are commercially available. The vector is introduced into the selected host cell, such as $E.$ $coli$ using methods that are widely known, and strains which are commonly available, e.g., $E.$ $coli$ strain HB101 or DH5α. Again, it will be appreciated that the polymerase gene product produced in this manner will be substantially free of other hepadnaviral components.

In vitro expression of the viral pol gene in cellular systems will result in the formation of a viral polymerase gene product. However, large amounts of the pol gene RNA transcript are not likely to be produced. The resulting polymerase gene product may be purified from host cells and other components of the expression system by common purification means, as described above for cell-free translation. In vitro expression kits are commercially available (e.g., from BioLabs, Beverly, Mass.) which contain instructions for in vitro expression and purification of the resultant proteins. The polymerase gene product produced by procaryotic or eucaryotic expression systems may be used immediately for activity assays, or may be stored for future use. Again, it should be apparent to those skilled in the art that assays for priming and reverse transcriptase activity of the gene product must be supplemented with the RNA template for synthesis of hepadnavirus minus strand DNA.

In accordance with the present invention, methods have been developed for measuring the DNA priming and reverse transcriptase activities of the hepadnavirus polymerase gene product. These methods rely on two key elements: (1) the availability, in accordance with the present invention, of adequate amounts of enzymatically active hepadnavirus polymerase gene product, and (2) the unexpected discovery, made in accordance with the present invention, that an RNA template for hepadnavirus minus strand DNA synthesis, comprising an initiation site for the minus strand synthesis, is required for priming and reverse transcriptase activity of the gene product.

The RNA transcript that actually encodes the polymerase gene product comprises the initiation site for minus strand DNA synthesis, and is preferred as the RNA template in the practice of the present invention. However, other templates (e.g., templates comprising only a portion of the pol gene transcript, or even synthetic templates) will also be useful in the methods of the invention, as long as they comprise at least some length of template sequence and an initiation site for minus strand DNA synthesis.

It should also be noted that magnesium ions are required for the catalytic functions of the polymerase gene product. Most DNA polymerases have been found to require magnesium or other divalent cations for catalytic activity. Hence, it should be appreciated by those skilled in the art that other divalent cations (including, but not limited to, magnanese) may be substituted for magnesium in the practice of the present invention.

It was previously known that dGTP is the first nucleotide triphosphate to be incorporated into the minus strand DNA synthesized from the hepadnavirus RNA pregenome. In accordance with the present invention, it has been determined that the formation of a covalent bond between the polymerase gene product and dGTP is the first step in minus strand DNA synthesis in DHBV and other hepadnaviruses having G as the first minus strand nucleotide. The formation of the aforementioned bond is referred to as "DNA priming activity".

A rapid in vitro assay for the DNA priming activity of the hepadnavirus polymerase gene product comprises combining the purified in vitro-synthesized gene product prepared as described above, with an appropriate template, e.g., the RNA transcript of the hepadnavirus pol gene having an initiation codon for minus strand DNA synthesis, and detectably labelled dGTP (or analog thereof), under conditions promoting the formation of a covalent bond between the gene product and the dGTP. It should be understood that, in the event a hepadnaviral template is used that does not incorporate dGTP as the first minus strand nucleotide, dGTP should be substituted with the appropriate nucleotide triphosphate (sometimes referred to herein as dNTP, N being any nucleotide), or analog thereof. However, for simplicity, the description below will exemplify dGTP as the first nucleotide incorporated into the DNA minus strand.

The priming assay is performed in a suitable biological buffer, such as 50 mM Tris-HCl (pH 7-8), 10 mM $MgCl_2$, 100 mM NaCl, 5 mM KCl, for time periods ranging from 5 to 60 minutes at temperatures between 20° C. and 45° C. In a preferred embodiment, in vitro translation reaction mix contains both the polymerase gene product and an appropriate RNA template, is utilized in the assay; therefore, additional RNA template need not be added. The dGTP added to the assay mixture may be detectably labelled by any common method known in the art. For example, in a preferred embodiment, $^{32}P$-dGTP is used. Other detectably labelled dGTP useful in the present invention includes $^{35}S$, $^{3}H$ or $^{14}C$-labelled dGTP, as well as biotinylated or otherwise modified dGTP analysis.

Because of the covalent binding of dGTP, the DNA priming activity results in the formation of a covalent complex comprising dGTP and the polymerase gene product. This complex remains intact even upon exposure to 1 M KOH at 55° C., and can be subjected to SDS polyacrylamide gel electrophoresis. The assay is based on measuring the amount of such a complex formed under pre-determined reaction conditions, as described above. Incorporation of labelled dGTP into the complex can be measured in a variety of ways, which will be readily apparent to those skilled in the art. For example, an aliquot of the assay mixture may be subjected to polyacrimide gel electrophoresis and autoradiography, if a radiolabel is used. Under these conditions, the complex is electrophoretically separated from the RNA template and other components of the reaction mixture, and can be visualized by autoradiography. The amount of dGTP incorporated into the complex may be quantitatively determined, e.g., by scanning densitometry. Alternatively, the protein-dGTP complex may be separated from the other components of the reaction mixture by immunological or other affinity methods, or by centrifugation. The amount of detectably labelled dGTP present in the separated complex may then be measured by various means, depending on the type of detectable labels used. These methods include, for example, liquid scintillation counting, spectrophotometry or fluorometry. Other methods for separating and measuring detectably labelled proteinaceous complexes are available, and should be apparent to one skilled in the art.

The above-described assay for priming activity of the hepadnavirus polymerase gene product may be modified to measure the gene product's reverse transcriptase activity. This is accomplished simply by adding, along with the detectably labelled dGTP the other nucleotide triphosphates necessary for DNA synthesis (i.e., dATP, dCTP, dTTP and analogs thereof). The reaction is carried out under conditions promoting the reverse transcriptase activity of the gene product. For example, reactions may be carried out at 30° C. to 45° C. for 5 to 60 minutes. Reverse transcriptase activity of the gene product results in the synthesis of a nascent DNA strand from the RNA template. This DNA strand is part of a covalent complex which also comprises the gene product. The complex is detectable, by way of the detectably labelled dGTP incorporated into the growing DNA strands by any conventional method allowing detection of labelled DNA, e.g., Southern blot analysis.

In an alternative embodiment of the assay for reverse transcriptase activity of the polymerase gene product, the detectable label may be incorporated in any one of the four nucleotide triphosphates added to the assay mixture. However, detectably labelled dGTP is preferred because it is the first nucleotide triphosphate to be incorporated into the nascent DNA strand in most hepadnaviruses, and as such, is covalently bound to the gene product, as described above. dCTP is least preferred as the detectably labelled nucleotide triphosphate because, in most hepadnaviruses, it is not incorporated in the growing DNA strand until several other nucleotide triphosphates have been incorporated. Therefore, use of this nucleotide triphosphate as a detectable label may underestimate the priming and reverse transcriptase activities of the viral gene product.

In yet another alternative embodiment, the reverse transcriptase assay may be performed using no labeled dNTPs. The nascent DNA strand may be labeled later, using common methods, such as nick-translation.

As described for the DNA priming activity assay above, the nucleotide triphosphates may be detectably labelled with a radioactive molecule, such as $^{32}P$, or they may be biotinylated or otherwise chemically modified so as to be detectable. Several methods are available to detect reverse transcriptase activity, including: (1) Southern blot analysis, (2) polyacrylamide gel electrophoresis, followed by autoradiography, as described above, (3) PCR amplification of the nascent DNA chain, and (4) primer extension. Methods to accomplish all of these detection techniques are well known in the art. As with the DNA priming activity assay described above, the complex comprising the polymerase gene product and the nascent DNA strand may be separated from the other components of the assay mixture. As described above, this may be accomplished by centrifugation. Preferably, though, the complex may be separated by affinity chromatography, and particularly advantageously by the use of antibodies recognizing the polymerase gene product. Once separated, the detectable label incorporated in the complex may be detected and quantified by several common means, depending on the type of detectable label utilized. These include liquid scintillation counting, spectrophotometry and fluorometry, among others.

The above-described rapid in vitro method of measuring the DNA priming and reverse transcriptase activities of the purified hepadnavirus polymerase gene product are described in greater detail in Examples 3 and 4 below.

The purified hepadnavirus polymerase gene product and the in vitro assay methods for measuring its priming and reverse transcriptase activities, as described above, are used to great advantage in the screening and development of anti-hepadnaviral agents. The gene product and assays provide an in vitro method for determining the effectiveness of potential anti-viral agent targeted to the pol gene or the polymerase gene product. Rapid, in vitro screening methods for anti-viral compounds directed to the polymerase gene product heretofore have been unavailable, due to the inability to obtain a substantially virus-free hepadnavirus gene product having biological activity.

Thus, potential anti-viral agents may be rapidly screened in vitro for their ability to inhibit the hepadnavirus polymerase gene product's priming activity, or reverse transcriptase activity, or both. For example, an assay mixture comprising the gene product, the RNA template and magnesium ions in a suitable biological buffer may be assembled. Aliquots of the mixture are then distributed into a series of test sample vessels containing compounds or agents suspected of having anti-viral activity. A control sample is also included, wherein an aliquot of the assay mixture is distributed to a sample tube containing no anti-viral agent. To measure the effect of the various potential anti-viral agents on the DNA priming activity of the gene product, reactions are initiated by the addition of detectably labelled dGTP, as described above, under conditions promoting formation of a covalent bond between the dGTP and the viral gene product. An identical series of assay samples may be assembled to test the effect of the potential anti-viral compounds on the reverse transcriptase activity of the gene product. In this instance, all four nucleotide triphosphates are added to the reaction mixture, as described above, for the reverse transcriptase activity assay. These samples are incubated under conditions which promote the elongation of the nascent DNA strand synthesized from the RNA template. Following the incubation periods, the amount of detectable label incorporated into the gene product-DNA complexes formed may be quantitated as described earlier. The lengths of the nascent DNA strands may also be observed, as an additional indication of the inhibitory capability of the potential anti-viral agent.

In this manner, many potential anti-viral compounds may be screened at one time in a rapid, in vitro assay. The assay may be conveniently adapted to large-scale screenings, e.g., in 96-well microtiter plates and the like. Moreover, quantitative results of the effect of each potential anti-viral agent are easily obtained, whereas heretofore, such results have been unobtainable.

In an alternative embodiment, the effect of various agents and processes directed toward the hepadnavirus pol gene itself may also be measured. For example, the rapid, in vitro assays may be used to measure the effect of in vitro mutagenesis of the pol gene or the RNA template. Thus, the effect of gene therapy, i.e., methods which alter or disrupt the formation of the polymerase gene product at the gene level, may be tested. Clearly, the enzymatically active hepadnavirus polymerase gene product and assay methods of the present invention provide a much-needed avenue for developing anti-hepadnaviral agents targeted to a critical step in the hepadnavirus life cycle.

The following examples are provided to describe the invention in further detail. These examples are intended merely to illustrate and not to limit the invention.

EXAMPLE 1

Sp6-Promoted In Vitro Transcription of the DHBV pol Gene

The duck hepatitis B virus (DHBV) pol gene was transcribed by SP6-promoted in vitro transcription, according to the following procedure. Plasmid p5.1Gal was utilized for in vitro transcription. This plasmid contains a complete genome of an infectious clone of DHBV, inserted downstream from an SP6 promoter. See, Mandart et al., J. Virol., 49: 782–92 (1984); Pugh et al., J. Virol., 62: 3513–16 (1988). A schematic diagram of the structure and orientation of the DHBV genome in p5.1Gal is shown in FIG. 1. FIG. 1 shows the structural arrangement of the polymerase open reading frame (open rectangle), which begins at the amino terminus with the terminal protein (TP) domain, followed by a spacer region and the DNA polymerase (RT) and RNaseH (RH) domains. The hatched vertical bar represents the initiation site for minus strand DNA synthesis at position 2537 on the DHBV genome (Mandart et al., supra). The filled in rectangle represents DHBV sequences flanking the polymerase gene. The location of the SP6 promoter used for transcription of the polymerase gene is shown upstream of the pol gene. The positions of the first two methionines and the last amino acid of the polymerase polypeptide are indicated at the bottom of the figure. The numbering of the positions shown on top of the figure corresponds to the published sequence of DHBV (Mandart et al., supra).

To transcribe the RNA template for the translation of the DHBV polymerase gene, p5.1Gal was linearized with the restriction endonuclease SalI. The transcription reaction was carried out as described in the protocol included in the MEGAscript kit (AMBION, Inc., Austin, Tex.). The transcription reaction contained 7 µl water, 2 µl 10X transcription buffer (AMBION, Inc., Austin, Tex.), 2 µl each of ATP, CTP, GTP and UTP (50 mM each), 1 µl linearized plasmid DNA, and 2 µl enzyme mix (SP6 RNA polymerase, AMBION, Inc.). The reaction was incubated for 3 hours at 37° C. Following the incubation, 1 µl of RNAse-free DNAseI (AMBION, Inc.) was added, and incubation was continued for 15 minutes at the same temperature. Reactions were stopped by adding 115 µl of RNAse-free distilled water and 15 µl of ammonium acetate stop solution (AMBION, Inc.) and mixing thoroughly. RNA was purified by extracting the reaction once with an equal volume of water or buffer-saturated phenol/chloroform, followed by precipitation of the RNA by adding 2.5 volumes ethanol and mixing well. Reactions were chilled for at least 15 minutes at −20° C., then microfuged for 15 minutes at maximum speed to pellet the P/gA. Supernatant was removed and the pellet resuspended in 1.5 µl of RNAse-free distilled water.

In vitro transcription of the DHBV polymerase gene resulted in the formation of a 3.1 kb RNA transcript. This transcript was utilized for in vitro translation to produce the polymerase gene product.

EXAMPLE 2

In Vitro Translation of RNA Transcript Encoding the DHBV Polymerase Gene Product The 3.1 kb RNA transcript produced by in vitro transcription, as described in Example i above, was used for in vitro translation to produce the DHBV polymerase gene product. The in vitro translation was carried out in a rabbit reticulocyte lysate in vitro translation system, according to methods provided by the commercial supplier (Promega Biotech, Madison, Wis.). The translation reaction contained the following ingredients: 14 µl rabbit reticulocyte lysate, 0.5 µl amino acid mixture (containing 1 mM of each amino acid), 0.5 µl RNasin (40 U/µl), 4 µl water and 1 µl RNA (1 mg/µl).

The RNA was incubated for 2 minutes at 65° C. before adding it to the reaction mixture. The reaction was incubated for 60–90 minutes at 30° C. The reaction was stopped with 2 µl of a solution containing cyclohexamide at a concentration of 0.2 mg/µl. In vitro translation samples were used either directly for the DNA priming/polymerase reactions (described in Examples 3 and 4 below) or they were frozen and stored at −70° C.

In vitro translation of the 3.1 kb RNA transcript produced by SP6-promoted transcription of the DHBV genome resulted in the formation of a major translation product of ~90 kd, as shown in FIG. 2. FIG. 2A shows the protein products obtained from in vitro translation reactions in the presence of $^{35}$S-methionine with RNA templates derived from p5.1Gal (See FIG. 1). The in vitro translation product of the 3.1 kb RNA encoding the DHBV polymerase gene product is shown in Lane 1, and the in vitro translation product from RNA purified from brome-mosaic (BMV), a control provided by the supplier of the translation kit, is shown in Lane 2. As can be seen from FIG. 2, Lane 1, in vitro translation of the 3.1 kb RNA transcript yielded a major protein product with a molecular weight of ~90 kd, as expected for the 836 amino acid-long polymerase gene product. See FIG. 1. The appearance of a second, more rapidly migrating protein product can be attributed to initiation at a second AUG codon, which is located 51 amino acids downstream of the first AUG of the polymerase open reading frame (Mandart et al., supra; see FIG. 1). It is believed that in vivo synthesis of the polymerase occurs from this second AUG (Chang et al., Nature, 337: 364–68 (1989); Schlicht et al., Cell, 5.6: 85–92 (1989)).

EXAMPLE 3

In vitro Assay for DNA Priming Activity of In Vitro-Synthesized DHBV Polymerase Gene Product The in vitro transcription/translation product prepared according to the method set forth in Examples 1 and 2 above was assayed for DNA priming activity, according to the following methods. 5 µl of the in vitro translation mixture (not labelled with $^{35}$S-methionine) was combined with 1 µl 10X reaction buffer (500 mM Tris-HCl pH 7.5, 100 mMMgCl$_2$, 150 mM NaCl), 2.5 µl water and 0.5 µl $^{32}$P-dGTP (400 Ci/mmol, 10 µCi/µl, Amersham). The reaction was incubated typically for 30 minutes at 30° C. The reaction was stopped by addition of 180 µl of protein loading buffer (50 mM Tris-HCl, pH 6.8, 5% β-mercaptoethanol, 2% SDS, 0.1% bromophenol blue and 10% glycerol). An aliquot (18 µl) of the solution was electrophoresed through a 10% SDS-containing polyacrylamide gel. The gel was then dried and autoradiographed.

The results of the DNA priming assay can be seen in FIG. 2A, Lanes 3 and 4. Lane 3 shows the results of the priming assay using the DHBV polymerase translation product; and Lane 4 shows a control assay, wherein the in vitro translation product of brome mosaic virus (BMV) was tested for DNA priming activity as a negative control (this translation product should possess no priming activity, and therefore no $^{32}$P-labelled bands should appear in Lane 4). As can be seen from FIG. 2A, the in vitro-synthesized DHBV polymerase gene product possesses the DNA priming activity ascribed to the polymerase gene product in vivo, as demonstrated by the incorporation of labelled dGTP into the protein, resulting in the visible band upon autoradiography. The in vitro translation product of BMV displays no such incorporation of dGTP.

EXAMPLE 4

In Vitro Assay for Measuring Reverse Transcriptase Activity of In Vitro-Synthesized DHBV Polymerase Gene Product The in vitro-synthesized DHBV polymerase gene product prepared as described in Examples 1 and 2 was assayed for RNA-dependent DNA polymerase activity (i.e., reverse transcriptase activity) according to the following procedures. The DNA polymerase assay reaction mixture was assembled exactly as described for the DNA priming reaction of Example 3, except that 1 µl of water was replaced with a solution containing dATP, dCTP and TTP (142 µM of each). The $^{32}$P-labelled dGTP could be replaced with $^{32}$p dATP or dTTP, if desired. If this is done, the appropriate changes should be made with the dNTP solution so that all 4 dNTPs are available in the reaction mixture. Reactions were incubated at 30° C. for 30 minutes and stopped by the addition of protein loading buffer, as described in Example 3 above.

In an alternative procedure, DNA was synthesized in the presence of all 4 dNTPs without $^{32}$P-labelled dNTP. The product of the completed DNA polymerization reaction was then purified by incubation with RNaseA (65 mg/µl final concentration) for 10 minutes at 37° C, and subsequently with SDS (0.6%) and proteinase K (1 mg/ml) for 1 hour at 45° C. DNA was extracted twice with phenol, once with phenolchloroform and with a solution of butanol:isopropanol (7:3) in 20 µl of TE (10 mM Tris-HCl, pH 8, 0.1 mM EDTA) containing 5 mg/μl RNaseA and incubated at 37° C. for 20 minutes. DNA was visualized with the Southern hybridization procedure, according to well known methods.

The results of the reverse transcriptase assay are shown in FIG. 2B. The polymerase reactions were incubated for 0, 5, 10 and 30 minutes (Lanes 1-4) at 30° C. and for 10 minutes at 22° C., 37° C. and 60° C. (Lanes 5-7). Reactions shown in FIG. 2B were carried out in the presence of $^{32}$P-dATP. The radioactivity (CPM) in the polymerase bands was quantitated with an imager system (AMBIS).

As can be seen in FIG. 2B, the rate of nucleotide incorporation into the growing DNA strand occurs in a time- and temperature-dependent fashion, as would be expected from an enzymatic reaction, and is not restricted to dGTP as a substrate. Moreover, additional slow-migrating products were observed extending upward from the position corresponding to the polymerase protein to the top of the polyacrylamide gel (Lane 3). It has been verified that these products represent polymerase proteins attached to longer DNA strands of varying lengths. Since the linkage between the protein and the first nucleotide of the growing DNA strand resisted boiling in SDS (and also incubation in 1 M KOH at 55° C., the results not shown herein), it is apparent that the protein-DNA bond is covalent.

The present invention is not limited to the embodiment specifically described and exemplified above, but is capable of variation and modification without departure from the scope of the appended claims.

What is claimed is:

1. A composition of matter comprising, in extracellular combination, a substantially virus-free hepadnavirus polymerase gene product and an RNA template for hepadnavirus minus strand DNA synthesis, said composition of matter having a DNA priming activity and a reverse transcriptase activity.

2. A composition of matter according to claim 1, wherein said hepadnavirus polymerase gene produce is that of Duck Hepatitis B virus.

3. A composition of matter according to claim 1, wherein said hepadnavirus polymerase gene product is produced by in vitro translation of an RNA molecule encoding said hepadnavirus polymerase gene product, said RNA molecule being produced by in vitro transcription of DNA molecule comprising said hepadnavirus polymerase gene.

4. A composition of matter according to claim 3, wherein said RNA molecule encoding said hepadnavirus polymerase gene product is produced by in vitro transcription of said hepadnavirus polymerase gene, inserted downstream from a bacteriophage promoter, utilizing a bacteriophage RNA polymerase specific for said promoter.

5. A composition of matter according to claim 1, wherein said promoter and said RNA polymerase are selected from the group of bacteriophages consisting of SP6, T7 and T3.

6. A composition of matter according to claim 3, wherein said hepadnavirus polymerase gene product is produced by in vitro translation of said RNA molecule encoding said gene product in a cell-free translation system.

7. A composition of matter according to claim 6, wherein said cell free translation system is selected from the group consisting of rabbit reticulocyte lysate system or wheat germ system.

8. A composition of matter according to claim 1, wherein said hepadnavirus polymerase gene product is produced by in vitro expression, in a cellular system, of a DNA molecule comprising said hepadnavirus polymerase gene.

9. A composition of matter according to claim 8, wherein said cellular in vitro expression system producing said hepadnavirus polymerase gene product is selected from the group consisting of a bacterial expression system and a eucaryotic expression system.

10. An enzymatically active composition of matter comprising, in extracellular combination, a hepadnavirus polymerase gene product and an RNA template for hepadnavirus minus strand DNA synthesis, both produced by expression, in a non-hepadnavirus system, of a purified and isolated DNA sequence encoding said hepadnavirus polymerase gene product.

11. An enzymatically active composition of matter according to claim 10, wherein the enzymatic activity comprises a DNA priming activity and a reverse transcriptase activity.

12. An enzymatically active composition of matter according to claim 10, wherein said purified and isolated DNA sequence encoding said polymerase gene product comprises a Duck Hepatitis B virus polymerase gene.

13. An enzymatically active composition of matter according to claim 10, wherein said purified and isolated DNA sequence encoding said polymerase gene product comprises a Human Hepatitis B virus polymerase gene.

14. An enzymatically active composition of matter according to claim 10, wherein said production of said RNA template and said hepadnavirus polymerase gene product by expression of said purified and isolated DNA sequence comprises:

a) placing said DNA sequence into an in vitro transcription vector, under the control of a bacteriophage promoter disposed within said vector;

b) exposing said DNA sequence placed into said in vitro transcription vector to a bacteriophage promoter RNA polymerase specific for said bacteriophage promoter disposed within said in vitro transcription vector, under conditions promoting in vitro transcription of said DNA sequence, thereby forming an RNA transcript which encodes said polymerase gene product, said RNA transcript also being said RNA template for hepadnavirus minus strand DNA synthesis; and c) translating said RNA transcript in a cell-free in vitro translation system under condition promoting the production of said hepadnavirus polymerase gene product, thereby forming said enzymatically active composition of matter.

15. An enzymatically active composition of matter according to claim 14, produced by in vitro transcription and translation of a Duck Hepatitis B polymerase gene disposed within plasmid p5.1Gal.

16. A composition of matter according to claim 1, wherein said RNA template for hepadnavirus minus strand DNA synthesis is produced by transcription of an entire hepadnavirus genome.

17. A composition of matter according to claim 1, wherein said RNA template for hepadnavirus minus strand DNA synthesis comprises a portion of an RNA transcript encoding said hepadnavirus polymerase gene product, said portion comprising an initiation site for hepadnavirus minus strand DNA synthesis.

18. A composition of matter according to claim 1, wherein said hepadnavirus polymerase gene produce is that of human hepatitis B virus.

* * * * *